United States Patent
Peters et al.

(10) Patent No.: US 10,667,786 B2
(45) Date of Patent: Jun. 2, 2020

(54) ULTRASOUND IMAGING APPARATUS AND METHOD FOR SEGMENTING ANATOMICAL OBJECTS

(71) Applicant: KONINKLIJKE PHILIPS N.V., Eindhoven (NL)

(72) Inventors: Jochen Peters, Eindhoven (NL); Amir Mohammad Tahmasebi Maraghoosh, Eindhoven (NL); Juergen Weese, Eindhoven (NL); Christian Buerger, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 314 days.

(21) Appl. No.: 15/540,297

(22) PCT Filed: Jan. 4, 2016

(86) PCT No.: PCT/EP2016/050021
§ 371 (c)(1),
(2) Date: Jun. 28, 2017

(87) PCT Pub. No.: WO2016/110463
PCT Pub. Date: Jul. 14, 2016

(65) Prior Publication Data
US 2017/0360396 A1    Dec. 21, 2017

Related U.S. Application Data

(60) Provisional application No. 62/100,136, filed on Jan. 6, 2015.

(30) Foreign Application Priority Data

Jan. 29, 2015 (EP) ...................................... 15152964

(51) Int. Cl.
A61B 8/14 (2006.01)
A61B 8/08 (2006.01)
(Continued)

(52) U.S. Cl.
CPC .............. *A61B 8/14* (2013.01); *A61B 8/5223* (2013.01); *G06T 7/0014* (2013.01); *G06T 7/12* (2017.01);
(Continued)

(58) Field of Classification Search
CPC ......... A61B 8/14; A61B 8/5223; A61B 8/468; G06T 7/75; G06T 7/0014; G06T 7/149;
(Continued)

(56) References Cited

U.S. PATENT DOCUMENTS 8,144,950 B2    3/2012  Peters et al.
8,260,586 B2    9/2012  Ecabert et al.
(Continued)

FOREIGN PATENT DOCUMENTS

JP    2005530546 A    10/2005
WO   WO2004000124 A1   12/2003

OTHER PUBLICATIONS

O. Ecabert, J. Peters, H. Schramm, C. Lorenz, J. von Berg, M. J. Walker, M. Vembar, M. E. Olszewski, K. Subramanyan, G. Lavi, and J. Weese: "Automatic Model-Based Segmentation of the Heart in CT images", IEEE Transactions on Medical Imaging, vol. 27(9), p. 1189-1201, 2008.

(Continued)

*Primary Examiner* — Sanjay Cattungal

(57) ABSTRACT

An ultrasound imaging apparatus (10) for segmenting an anatomical object in a field of view (29) of an ultrasound acquisition unit (14) is disclosed. The ultrasound imaging apparatus comprises a data interface (32) configured to receive a two-dimensional ultrasound data (30) of the object
(Continued)

in the field of view in an image plane from the ultrasound acquisition unit and to receive a three-dimensional segmentation model (46) as a three-dimensional representation of the object from a segmentation unit (36). An image processor (34) is configured to determine a two-dimensional segmentation model (50) on the basis of the three-dimensional segmentation model and a segmentation plane (48), wherein the segmentation plane and an image plane of the two-dimensional ultrasound data correspond to each other. The image processor is configured to adapt a contour of the two-dimensional segmentation model to the two-dimensional ultrasound data on the basis of pattern detection and where the image processor is configured to provide annotated two-dimensional image data (42) on the basis of the two-dimensional ultrasound data and the adapted segmentation model aligned to the two-dimensional ultrasound data.

11 Claims, 7 Drawing Sheets

(51) Int. Cl.
| | | |
|---|---|---|
| *G06T 7/12* | (2017.01) | |
| *G06T 7/149* | (2017.01) | |
| *G06T 7/73* | (2017.01) | |
| *G06T 7/00* | (2017.01) | |
| *A61B 8/00* | (2006.01) | |

(52) U.S. Cl.
CPC ............... *G06T 7/149* (2017.01); *G06T 7/75* (2017.01); *A61B 8/468* (2013.01); *G06T 2200/04* (2013.01); *G06T 2207/10132* (2013.01); *G06T 2207/10136* (2013.01); *G06T 2207/20128* (2013.01); *G06T 2207/30004* (2013.01); *G06T 2207/30244* (2013.01); *G06T 2219/004* (2013.01)

(58) Field of Classification Search
CPC ................. G06T 7/12; G06T 2219/004; G06T 2207/10136; G06T 2207/20128; G06T 2207/30244; G06T 2207/30004; G06T 2207/10132; G06T 2200/04
See application file for complete search history.

(56) References Cited

U.S. PATENT DOCUMENTS

| | | | |
|---|---|---|---|
| 9,129,387 B2 | 9/2015 | Ecabert et al. | |
| 2002/0102023 A1* | 8/2002 | Yamauchi | G06T 7/149 |
| | | | 382/199 |
| 2003/0236462 A1 | 12/2003 | Salgo et al. | |
| 2006/0159341 A1 | 7/2006 | Pekar et al. | |
| 2007/0167760 A1* | 7/2007 | Kim | G06K 9/3233 |
| | | | 600/437 |
| 2008/0069436 A1* | 3/2008 | Orderud | G06T 7/20 |
| | | | 382/154 |
| 2009/0115798 A1 | 5/2009 | Weese | |
| 2010/0198072 A1* | 8/2010 | Abe | A61B 8/08 |
| | | | 600/443 |
| 2012/0065510 A1 | 3/2012 | Snare et al. | |
| 2013/0182924 A1* | 7/2013 | Lause | G06T 7/0014 |
| | | | 382/131 |
| 2013/0324841 A1* | 12/2013 | Kamen | A61B 8/0841 |
| | | | 600/424 |
| 2014/0105473 A1* | 4/2014 | Kim | G06T 7/149 |
| | | | 382/128 |
| 2014/0185895 A1* | 7/2014 | Swamy | A61B 8/0866 |
| | | | 382/131 |
| 2014/0193053 A1* | 7/2014 | Kadoury | G06T 15/08 |
| | | | 382/131 |
| 2014/0233818 A1* | 8/2014 | Thiruvenkadam | G06T 7/174 |
| | | | 382/131 |
| 2014/0341449 A1* | 11/2014 | Tizhoosh | A61B 6/5217 |
| | | | 382/128 |
| 2015/0016704 A1 | 1/2015 | Weese et al. | |
| 2015/0182191 A1* | 7/2015 | Caluser | A61B 5/055 |
| | | | 600/440 |
| 2016/0012582 A1 | 1/2016 | Mauldin et al. | |
| 2016/0143576 A1* | 5/2016 | Symon | A61B 8/085 |
| | | | 600/411 |
| 2017/0181730 A1* | 6/2017 | Ardon | A61B 8/0866 |

OTHER PUBLICATIONS

J. Peters, O. Ecabert, C. Meyer, R. Kneser, J. Weese: "Optimizing boundary detection via Simulated Search with applications to multi-modal heart segmentation", Medical Image Analysis 14 (2010), p. 70-84.

* cited by examiner

ULTRASOUND IMAGING APPARATUS AND METHOD FOR SEGMENTING ANATOMICAL OBJECTS

This application is the U.S. National Phase application under 35 U.S.C. § 371 of International Application No. PCT/EP2016/050021, filed on Jan. 4, 2016, which claims the benefit of Provisional Application Ser. No. 62/100,136 filed Jan. 6, 2015 and EP Application Serial No. 15152964.1 filed Jan. 29, 2015. These applications are hereby incorporated by reference herein.

FIELD OF THE INVENTION

The present invention relates to an ultrasound imaging apparatus for segmenting anatomical objects in a field of view of an ultrasound acquisition unit. The present invention further relates to a method for segmenting an anatomical object in a field of view of an ultrasound acquisition unit. In particular, the present invention relates to image processing and segmentation of anatomical objects in a scanned volume of a patient. The present invention further relates to a computer program comprising program code means for causing a computer to carry out the steps of the method according to the invention when said computer program is carried out on a computer.

BACKGROUND OF THE INVENTION

In the field of medical imaging systems it is generally known to combine different images of a patient acquired by identical or different medical analysis systems in order to improve the diagnostic possibilities. In particular, ultrasound systems are known which combine ultrasound images with pre-operative image data of a patient derived from different imaging systems.

Ultrasound imaging systems can further combine pre-defined models of the anatomical structure scanned by the ultrasound probe or segmentation data with the images derived from the acquired ultrasound data in order to provide segmented images on the basis of the anatomical model and the ultrasound image data. A corresponding system is e.g. known from US 2012/0065510 A1.

During an ultrasound image assisted medical procedure such as a biopsy and/or branchytherapy, a real-time image and a corresponding real-time segmentation of anatomical objects i.e. a definition of a volume or a surface of an anatomical object in the field of view of the ultrasound probe can provide several advantages.

Conventional anatomical segmentation techniques require a clear contrast between different tissues visible in the provided image data such as magnet resonance tomography (MRT) or computer tomography (CT). However a majority of the known segmentation techniques have a reduced performance for ultrasound imaging systems, since the segmentation model cannot properly be aligned to the ultrasound images which have a poor signal-to-noise ratio. Usually a prior information about the shape of the anatomical structure to be segmented can improve the segmentation of the anatomical structures in the ultrasound images and these techniques are typically applied to three-dimensional data which require a large computation effort so that these techniques are typically expensive and cannot be applied to real-time applications.

In some further known biopsy and/or branchytherapy applications two-dimensional image data is acquired and on the basis of a position sensor reconstructed into a regular three-dimensional voxel array which is used for segmentation of anatomical objects.

The disadvantage of the known techniques for segmenting anatomical objects in ultrasound image data is that the previously determined three-dimensional segmentation models do not consider deformation of the anatomical objects during the analysis. The computational effort for aligning the segmentation model to real-time three-dimensional ultrasound image data makes three-dimensional segmentation in real-time during the intervention difficult. Furthermore, acquiring three-dimensional data during the intervention is complex so that typically only two-dimensional data is acquired during the intervention.

SUMMARY OF THE INVENTION

It is an object of the present invention to provide an improved ultrasound imaging apparatus which can segment anatomical objects in ultrasound data with high precision and low technical effort. It is further an object of the present invention to provide a corresponding method for segmenting anatomical objects in ultrasound data. It is finally an object of the present invention to provide a computer program for implementing such method and a non-transitory memory for storing such computer program.

In a first aspect of the present invention an ultrasound imaging apparatus is provided for segmenting an anatomical object in a field of view of an ultrasound acquisition unit, comprising:

a data interface configured to receive two-dimensional ultrasound data of the object in the field of view in an image plane from the ultrasound acquisition unit and to receive a three-dimensional segmentation model as a three-dimensional representation of the object from a segmentation unit, an image processor configured to determine a two-dimensional segmentation model on the basis of the three-dimensional segmentation model and a segmentation plane, wherein the segmentation plane and an image plane of the two-dimensional ultrasound data correspond to each other, and wherein the image processor is configured to deformably adapt a contour of the two-dimensional segmentation model to the two-dimensional ultrasound data on the basis of pattern detection and wherein the image processor is configured to provide annotated two-dimensional image data on the basis of the two-dimensional ultrasound data and the segmentation model adapted to the two-dimensional ultrasound data.

According to another aspect of the present invention a method for segmenting an anatomical object in a field of view of an ultrasound acquisition unit is provided comprising the steps of:

receiving two-dimensional ultrasound data in an image plane of the object in the field of view from the ultrasound acquisition unit;

receiving a three-dimensional segmentation model as a three-dimensional representation of the object from a segmentation unit, determining a two-dimensional segmentation model on the basis of the three-dimensional segmentation model and a segmentation plane intersecting the three-dimensional segmentation model, wherein the segmentation plane and the image plane correspond to each other, deforming a contour of the two-dimensional segmentation model to the two-dimensional ultrasound data on the basis of pattern detection in the two-dimensional ultrasound data, and providing annotated two-dimensional image data on the basis of the two-dimensional ultrasound data and the two-dimensional segmentation model adapted to the two-dimensional ultrasound data.

According to another aspect a computer program is provided comprising program code means for causing a computer to carry out the steps of the method according to the invention when said computer program is carried out on a computer.

According to another aspect a storing medium is provided for storing the computer program according to the present invention.

Preferred embodiments of the invention are defined in the dependent claims. It shall be understood that the claimed method has similar and/or identical preferred embodiments as the claimed device and as defined in the dependent claims.

The present invention is based on the idea to derive a two-dimensional segmentation model of an anatomical object from a three-dimensional segmentation model and a segmentation plane which corresponds to a cutting plane or an intersecting plane of the three-dimensional representation of the segmentation model, wherein an image plane of the acquired ultrasound data corresponds to the segmentation plane so that the corresponding two-dimensional segmentation model can be adapted to the two-dimensional ultrasound data with low computational effort and within a reduced time frame. In order to achieve a precise adaptation or correlation of the two-dimensional segmentation model and the two-dimensional ultrasound data, the two-dimensional segmentation model is further adapted to the two-dimensional ultrasound data by deforming a contour on the basis of pattern detected in the ultrasound data. After the adaptation of the model to the ultrasound data, a correspondingly annotated two-dimensional image can be provided. In the annotated two dimensional image data, different image portions like different pixels are annotated or labeled as different anatomical features on the basis of the two dimensional segmentation model. In addition or alternatively, the surface pixels of the anatomical object can be annotated to provide a contour for visual display. Hence, the anatomical object can be segmented in the ultrasound data received from the ultrasound acquisition unit with low computational effort within a short time frame and with high precision.

On the basis of the so reduced computational effort the adaptation of a segmentation model and ultrasound data segmentation of the anatomical object can in particular be provided for a live image stream of the ultrasound data so that the imaging apparatus and the imaging method can, e.g., be used for biopsy or branchytherapy operations or other image-guided interventions.

In a preferred embodiment, the segmentation unit comprises a data interface configured to receive three-dimensional medical image data of the object, and wherein the segmentation unit is configured to adapt a predefined three-dimensional segmentation model of the anatomical object on the basis of the three-dimensional medical image data prior to the two-dimensional imaging procedure. This is a possibility to obtain a precise and a detailed segmentation that can be provided as the three-dimensional representation of the object. The adapted predefined three-dimensional segmentation model is a patient specifically adapted three-dimensional representation of the anatomical object and forms the three-dimensional segmentation. The predefined three-dimensional segmentation model and a patient specific three-dimensional segmentation is used in the following during processing of the two-dimensional segmentation.

This enables to utilize knowledge of general anatomical features and the image appearance of the object in the field of view derived from the predefined three-dimensional segmentation model. As a result, we obtain a two-dimensional segmentation model encoding the knowledge about anatomical features and the image appearance. This two-dimensional model only needs to be adapted to the individual anatomical features and image appearance of the patient.

In a further preferred embodiment, the segmentation unit is configured to provide the adapted three-dimensional segmentation model to the data interface.

In a preferred embodiment, the three-dimensional segmentation model and/or the two-dimensional segmentation model include a plurality of model elements forming a representation of the anatomical object and wherein anatomical information and/or pattern information are assigned to the model elements. The model elements preferably form line elements or surface elements of the two-dimensional segmentation model or the three-dimensional segmentation model. This is a possibility to improve the adaptation of the contour of the two-dimensional segmentation model and to improve the information provided in the annotated image data, since the segmentation model includes more information than the mere outer shape so that the probability of a misalignment or a wrong segmentation can be reduced.

In a preferred embodiment, the image processor is configured to deformably adapt a contour of the two-dimensional segmentation model to the ultrasound data on the basis of the anatomical information and/or the pattern information. This is a further possibility to improve the precision of the identification and the alignment, since the additional information like the anatomical information and/or the pattern information can be utilized in addition to the shape of the three-dimensional representation of the anatomical object. The model elements may comprise a pattern information so that the respective elements can be aligned to correspondingly formed pattern in the ultrasound image data, wherein not only edges are detected in the ultrasound image data but also local image intensities or other image patterns are taken into account.

In a preferred embodiment, the pattern information comprise ultrasound data intensity information of the object, wherein the image processor is configured to adapt a contour of the two-dimensional segmentation model to corresponding patterns in the two-dimensional ultrasound data. This is a possibility to improve the alignment of the segmentation model to the ultrasound image data, since the alignment is not (only) based on simple edge detection but based on more general pattern information in the ultrasound image data. This is a possibility to improve the reliability of the alignment in general.

In a preferred embodiment, the pattern information comprises intensity values and/or intensity gradients to which the model elements are aligned. This is a possibility to further improve the adaptation or the deformation of the shape of the two-dimensional segmentation model since further intensity or contrast information in the ultrasound data can be utilized to segment the anatomical object in the field of view. In this respect the intensity information may be an intensity on one or the two opposite sides of the model elements to which the model elements should be aligned so that not only the edge detection is utilized but also the intensity information of the adjacent tissue.

In a preferred embodiment, the image processor is configured to display the anatomical information in the annotated image data. This is a possibility to further improve the reliability of the object segmentation, since the user can check whether the respective anatomical feature of the segmentation is properly aligned to the anatomical features in the ultrasound image.

In a preferred embodiment, the ultrasound imaging apparatus further comprises a position determining unit for determining a position and a viewing direction of the ultrasound acquisition unit and for determining the image plane of the two-dimensional ultrasound data, wherein the image processor is configured to determine the segmentation plane corresponding to the determined image plane. This is a possibility to determine the two relevant planes i.e. the image plane of the two-dimensional ultrasound data and the segmentation plane corresponding to each other, so that an alignment of the two-dimensional segmentation model and the two-dimensional ultrasound data can be achieved with low computational effort, high precision, and within a short time frame. The image plane is determined by the position determining unit and on the basis of the so determined image plane, the segmentation plane is determined so that the three-dimensional segmentation model can be reduced to the corresponding two-dimensional segmentation model in the segmentation plane and the two-dimensional segmentation model can be applied to the ultrasound image in the image plane.

In an alternative embodiment, the segmentation plane is predefined in relation to the three-dimensional segmentation and the image plane is adapted to the predefined segmentation plane. This is a possibility to determine the plane in which the ultrasound image should be acquired and to adapt the respective image plane to the so-defined segmentation plane so that a user can define the image to be captured prior to the imaging procedure.

In a further embodiment, the ultrasound imaging apparatus comprises a user interface, wherein the segmentation plane is predefined by the user via the user interface in relation to the three-dimensional segmentation model. This is a possibility to select the segmentation plane prior to the imaging and to adapt the image plane to the preselected segmentation plane. This allows to select the segmentation plane without the need of acquiring and segmenting a three-dimensional image before the start of two-dimensional imaging.

In a further preferred embodiment, the data interface is configured to receive the two-dimensional ultrasound data of the anatomical object in the field of view from the ultrasound acquisition unit as a continuous data stream. This is a possibility to utilize live images of the anatomical object which are received in a continuous data stream so that a biopsy or a branchytherapy or some other intervention can be performed on the basis of the respective segmentation of the anatomical object.

As mentioned above, the present invention provides a possibility to reduce the computational effort and the necessary time frame for segmenting an anatomical object. This is enabled by using two-dimensional instead of three-dimensional ultrasound data, since the two-dimensional segmentation model is determined on the basis of a three-dimensional segmentation model that is cut or intersected along the segmentation plane which corresponds to the image plane of the two-dimensional ultrasound data to which the two-dimensional segmentation model shall be adapted. Further, the precision of the alignment can be improved since the shape of the so determined two-dimensional segmentation model can be deformably adapted to the ultrasound data on the basis of pattern detection in the ultrasound data. In other words a coarse alignment is achieved by the correlation of the respective segmentation plane and the image plane and a fine correlation or adaptation is achieved by the adaptation of the shape of the segmentation model so that also a deformation of the anatomical object during the analysis can be considered.

In addition, the present invention allows to use only two-dimensional image data with a dynamically defined orientation with the organ to be segmented. If three-dimensional data and a resulting segmentation is not available, the desired image plane may be defined using a graphical user interface (GUI) where the user can interactively rotate and shift a virtual plane in relation to a phantom drawing of the three-dimensional organ surface representing the shape of the segmentation model. In this way, a two-dimensional segmentation model can be derived from the three-dimensional segmentation model by means of the plane defined by the user via the GUI. The desired viewing direction within the desired plane orientation may be defined by an advanced GUI (e.g., where the user can position the ultrasound transducer or draw a scan acquisition direction).

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
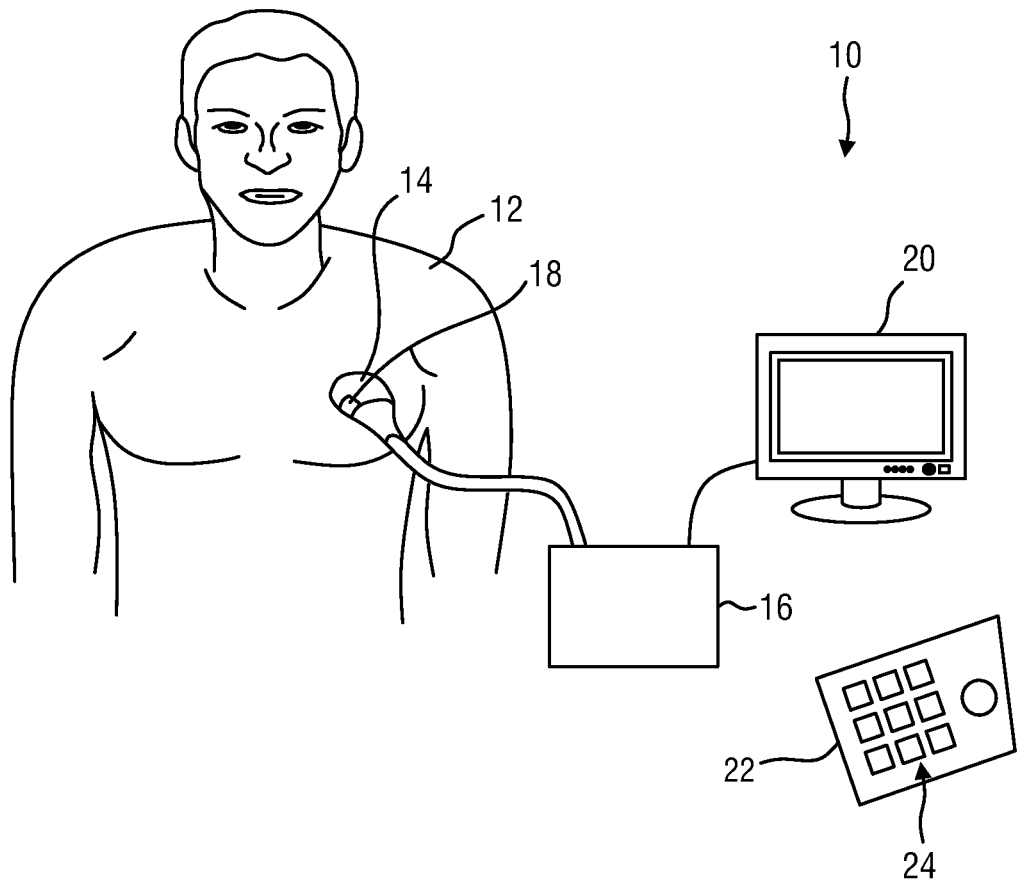
FIG. 1 shows a schematic representation of a medical imaging system in use to scan a volume of a patient's body.

FIG. 1 shows a schematic illustration of an ultrasound imaging apparatus 10 according to an embodiment, in particular a medical ultrasound two-dimensional imaging system. The ultrasound imaging apparatus 10 is applied to inspect a volume of an anatomical site, in particular an anatomical site of a patient 12. The ultrasound imaging apparatus 10 comprises an ultrasound probe (or ultrasound acquisition unit) 14 having at least one transducer array having a multitude of transducer elements for transmitting and/or receiving ultrasound waves. The transducer elements are arranged in an array so that the ultrasound probe 14 can determine two-dimensional ultrasound data in a field of view in an image plane of the anatomical site of the patient 12.

The ultrasound imaging apparatus 10 comprises a control unit 16 that controls the ultrasound probe 14 and the acquisition of the ultrasound data. As will be explained in further detail below, the control unit 16 controls not only the acquisition of ultrasound data via the ultrasound probe but also signal and image processing that form the ultrasound images out of the echoes of the ultrasound beam received by the transducer array of the ultrasound probe 14. The control unit 16 further segments anatomical objects in the field of view of the ultrasound probe 14 by aligning the image plane of the ultrasound probe 14 and a segmentation plane of a segmentation of the respective anatomical object and aligns the segmentation and the ultrasound image data as described in detail below.

The ultrasound imaging apparatus 10 further comprises a position determining unit 18, which determines a position and a viewing direction of the ultrasound probe 14 in order to determine the spatial orientation of an image plane of the ultrasound data acquired by the ultrasound probe 14. The position determining unit 18 may be incorporated in the ultrasound probe 14 as shown in FIG. 1 or, alternatively may be provided as a separate positioning determining unit such as an electromagnetic tracking unit.

The ultrasound imaging apparatus 10 further comprises a display 20 for displaying an image including the ultrasound data and the respectively aligned segmentation model for defining a volume or a surface of the anatomical object in the field of view of the ultrasound probe 14. Further, an input device 22 may be provided that may comprise keys or a keyboard 24 for providing a user input. The input device 22 may be connected to the display 20 or directly to the control unit 16.

Figure 2:
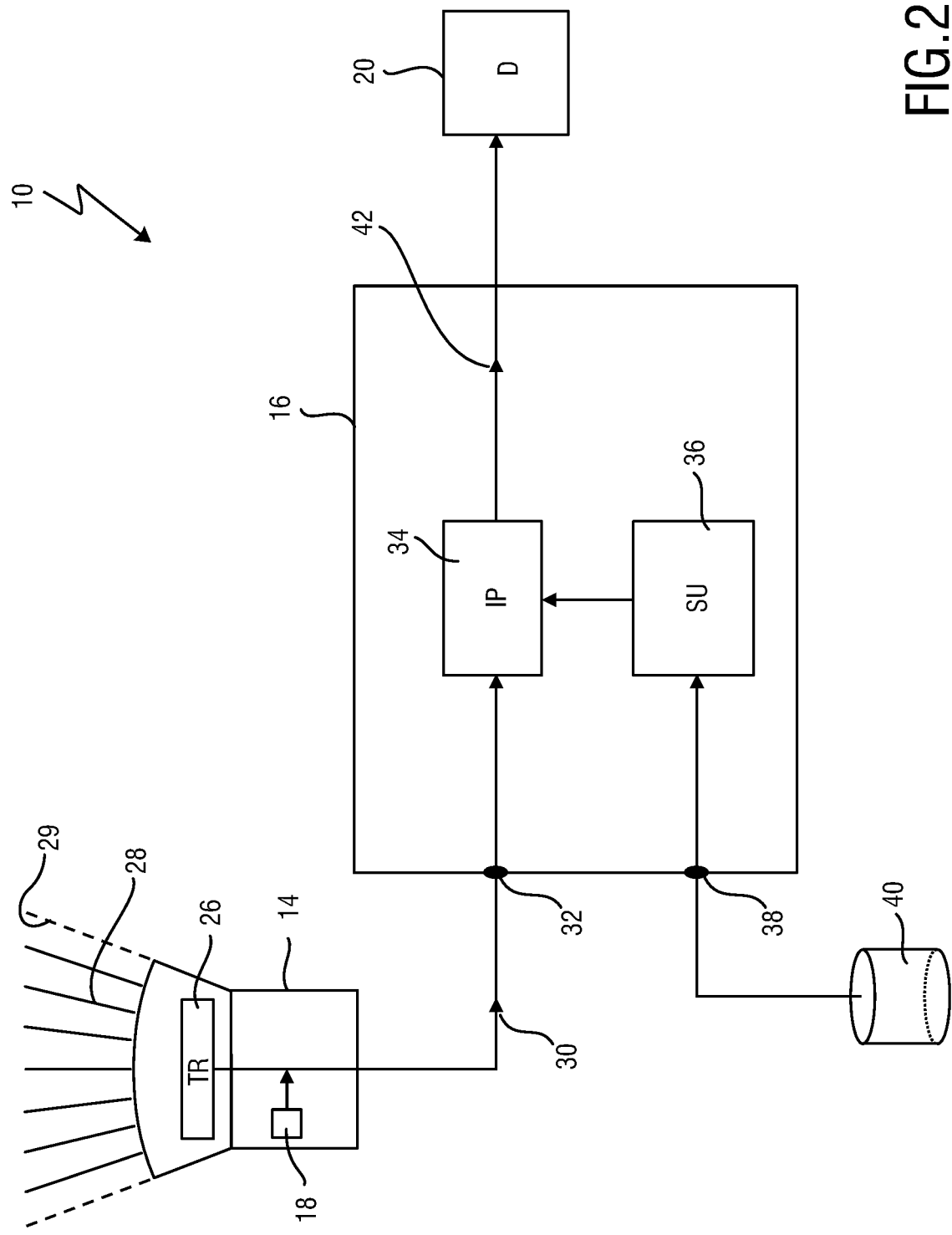
FIG. 2 shows a schematic block diagram of an embodiment of the ultrasound imaging apparatus.

FIG. 2 shows a detailed schematic diagram of the ultrasound imaging apparatus 10 shown in FIG. 1. Identical elements are denoted by identical reference numerals, wherein here merely the differences are described in detail.

The ultrasound probe 14 comprises the transducer array 26 for transmitting and receiving ultrasound waves 28 in a field of view 29. The ultrasound probe 14 comprises the position determining unit 18 for determining a position and a viewing direction of the ultrasound probe 14 or the transducer array 26. The position determining unit 18 determines on the basis of the position and the viewing direction of the ultrasound probe 14 or the transducer array 26 an image plane of ultrasound data 30 captured by the transducer array 26 and provided to the control unit 16. The ultrasound data is two-dimensional ultrasound data, wherein two-dimensional image data can be derived from the two-dimensional ultrasound data. The ultrasound data is preferably a continuous data stream and provided as live image data.

The ultrasound probe 14 is connected to an input interface 32 of the control unit 16 to provide the ultrasound data 30 and the position and the viewing direction of the ultrasound probe 14 or the image plane of the ultrasound data 30 to the control unit 16.

The control unit 16 comprises in general an image processor 34, which is connected to the data interface 32 for receiving the ultrasound data 30 and the position and the viewing direction or the image plane from the position determining unit 18. The control unit 16 further comprises a segmentation unit 36 which is connected to a data interface 38 for receiving medical image data from a database 40 or an additional medical imaging apparatus 40.

The image processor 34 in general determines an ultrasound image on the basis of the ultrasound data 30 and provides the image data 42 to the display 20 in order to display the image data to the user.

The segmentation unit 36 receives three-dimensional medical image data from the database or the external medical imaging apparatus 40 as image data of the patient 12 and provides a patient specific segmentation model of certain anatomical objects of the patient 12 on the basis of predefined segmentation models corresponding to the respective anatomical objects. The external medical imaging apparatus 40 may be an MRT, a CT or a 3D ultrasound apparatus. The patient specific segmentation model provided by the segmentation unit comprises an adapted mesh of the predefined model adapted to the patient's anatomy and in the patient's coordinate system. The so determined three-dimensional segmentation model is provided by the segmentation unit 36 to the image processor 34.

The image processor 34 receives the two-dimensional ultrasound data 30 and the respective image plane having the same coordinate system as the three-dimensional segmentation model received from the input interface 32. On the basis of the image plane in which the two-dimensional ultrasound data is captured, a segmentation plane is determined and the three-dimensional segmentation model is cut or intersected along the segmentation plane so that the three-dimensional segmentation model is reduced to a two-dimensional segmentation model representing a contour or a shape of the respective anatomical object in the segmentation plane.

During the transformation of the three-dimensional segmentation model to the two-dimensional segmentation model intersected along the segmentation plane, additional anatomical information and/or pattern information of the corresponding three-dimensional segmentation model is also transformed and the corresponding two-dimensional segmentation model is created. In this two-dimensional segmentation model, each of the model elements like segmentation lines are associated with additional information about the anatomical features and/or pattern information of the corresponding ultrasound image.

The three-dimensional segmentation model is based on a predefined segmentation model which is adapted to the respective anatomical object of the patient 12 on the basis of the three-dimensional medical image data. It is formed by a mesh of triangles, wherein each triangle includes boundary information, anatomical information or pattern information corresponding to the anatomical object and the respective image data associated with the anatomical object. During the transformation of the three-dimensional segmentation model to the two-dimensional segmentation model, the triangles of the mesh are transformed to corresponding lines of the contour in the two-dimensional segmentation model, wherein the anatomical information, the boundary information and/or the pattern information associated with the triangles is also transformed to the two-dimensional segmentation model, so that the respective information is also associated with the lines of the two-dimensional segmentation model.

The image processor 34 is configured to combine the two-dimensional segmentation model and the ultrasound image data 30 in order to provide annotated image data 42 which is provided to the display unit 20. The annotated image data 42 comprises ultrasound image data of the anatomical object and the contour data or the shape of the anatomical object superposed on the ultrasound image data in order to identify the anatomical object in the combined image data 42. In the annotated image data 42 the different image portions or pixels are annotated or labeled as a certain anatomical feature, in order to identify or label the anatomical object. The contour or shape of the two-dimensional segmentation model is adapted to the ultrasound image data by deforming the model contour on the basis of pattern detection. Hence, a movement or a deformation of an anatomic object such as an organ can be considered and the respective anatomical object can be identified or labeled precisely with low technical effort. During the adaptation or deformation step the anatomical information, the boundary information and/or the pattern information of the line segments of the two-dimensional segmentation model is utilized to align the two-dimensional segmentation model to the ultrasound image data and, further, the information is used to adapt the shape of the two-dimensional segmentation model to the anatomical object in the ultrasound data on the basis of pattern detection, contrast information and/or contrast gradients in the ultrasound image data. Further, other mapped model parameters like energy weights balancing mesh stiffness versus image forces can be utilized to adapt the contour or the shape of the two-dimensional segmentation model to the image data.

Since the segmentation plane and the respective two-dimensional segmentation model can be determined with low technical effort and low computational effort and since the adaptation or deformation of the two-dimensional segmentation model to the ultrasound image data 30 can be performed with low computational effort and in a short time frame, the adaptation of the two-dimensional segmentation model can also be applied to live image data which is provided as a continuous data stream to the image processor 34. Hence, the segmentation of the anatomical object can also be applied to ultrasound live image applications.

Figure 3:
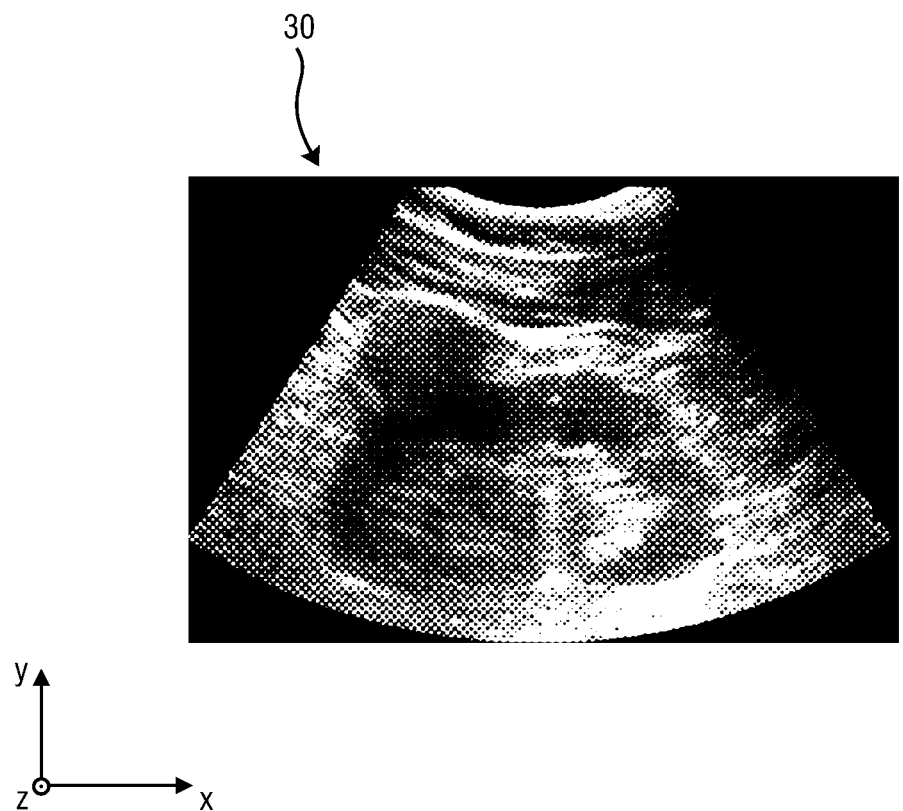
FIG. 3 shows a two-dimensional ultrasound image captured by an ultrasound probe.
Figure 4:
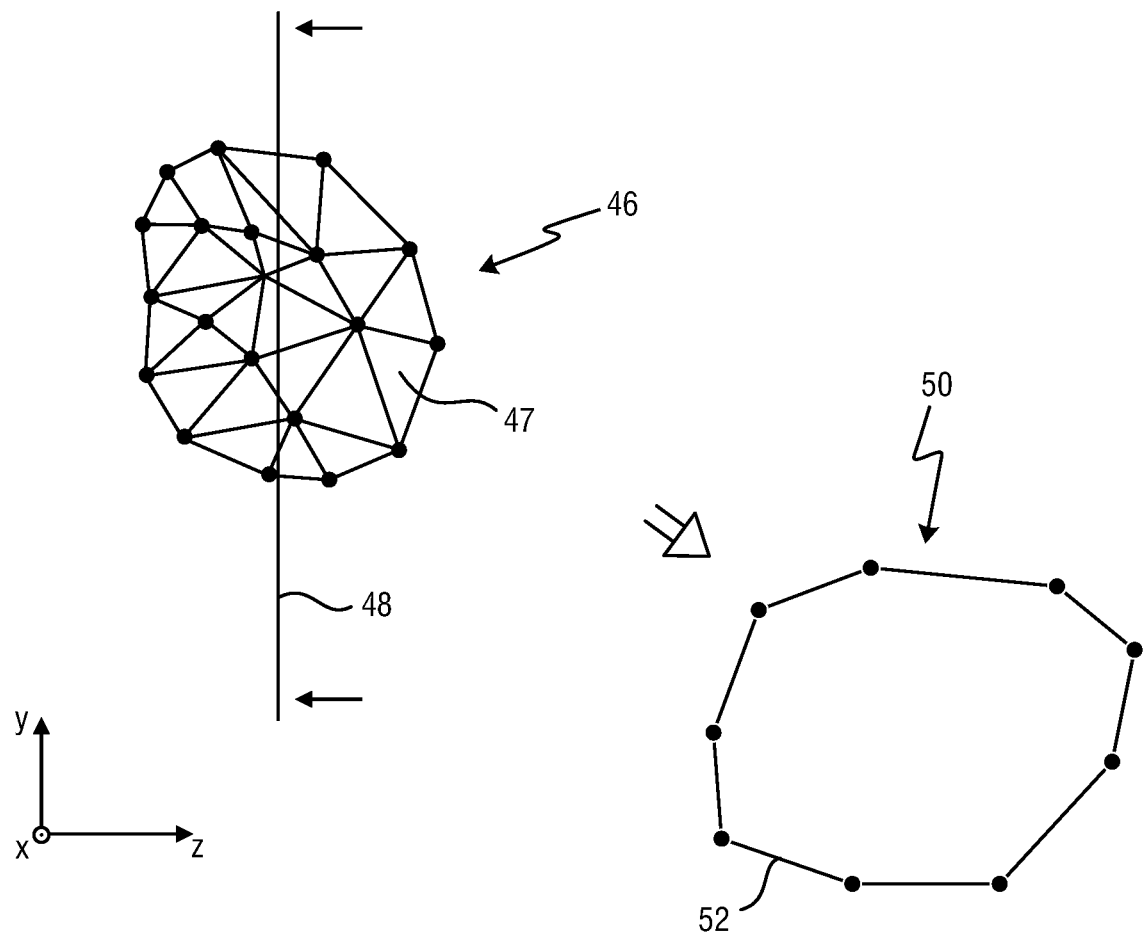
FIG. 4 shows a schematic diagram of a segmentation of an anatomical object.

FIG. 3 shows a schematic illustration of the ultrasound data 30 in the form of an ultrasound image captured along the image plane, which is in this particular case the yx-plane in the cartesian coordinate system indicated in FIG. 3. The so determined image plane determined by the position determining unit 18 is provided to the image processor 34 so that the image processor 34 can determine the segmentation plane for segmentation of the anatomical object in the field of view 29 as described in the following. In FIG. 4, the three-dimensional segmentation obtained by adapting a corresponding segmentation model is schematically shown as a mesh 46 of triangles 47. The three-dimensional segmentation model 46 is determined on the basis of a corresponding, predefined three-dimensional segmentation model adapted to the anatomical object of the patient 12 on the basis of the three-dimensional medical image data received from the database 40 or the medical image apparatus 40 as described above and provided by the segmentation unit 36 to the image processor 34. The image processor 34 determines a segmentation plane 48 corresponding to the coordinates of the image plane provided by the position determining unit 18 as shown in FIG. 4, wherein the segmentation plane corresponds to the yx-plane in the cartesian coordinate system as indicated in FIG. 4. The segmentation plane 48 defines a cutting plane or an intersection plane of the three-dimensional segmentation model 46, wherein the image processor 34 is configured to determine two-dimensional segmentation model 50 on the basis of the three-dimensional segmentation model 46, the corresponding three-dimensional segmentation model, and the segmentation plane 48 as shown in FIG. 4. The two-dimensional segmentation model 50 also defines a two-dimensional segmentation in the form of a two-dimensional contour or a shape of the anatomical object to be segmented.

The two-dimensional segmentation model 50 comprises different line segments 52 corresponding to the triangles 47 of the three-dimensional segmentation model 46 cut by the segmentation plane 48. The triangles 47 of the adapted three-dimensional segmentation model 46 each comprises additional anatomical information, boundary information or pattern information, wherein the pattern information may include image contrast information, image intensity information, intensity gradients which are expected in the ultrasound image data 30. The pattern information may be for example intensities on both sides of the triangle expected in the respective ultrasound image. The information associated with each of the triangles of the three-dimensional segmentation model 46 is transformed to the two-dimensional segmentation model 50, so that each of the line segments 52 comprises the additional information and can be aligned accordingly to the ultrasound image. Hence, the line segments 52 are e.g. not only adapted to the image data on the basis of edge detection but also correspondingly aligned to image intensity on both sides of the line segments 52.

Figure 5:
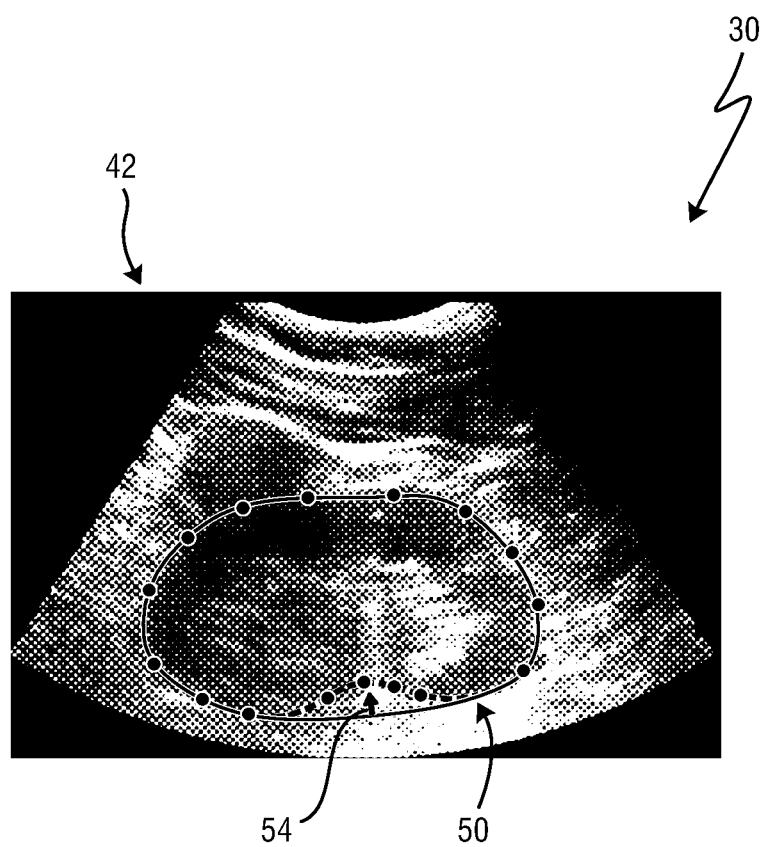
FIG. 5 shows an alignment of the segmentation model and the ultrasound image in order to segment an anatomical object in the field of view.

The alignment of the two-dimensional segmentation model 50 is schematically shown in FIG. 5, wherein the segmentation model is superimposed and aligned to the anatomical object in the ultrasound image data 30. In a further step, an annotated image 42 is provided wherein each pixel is annotated or labeled as a certain anatomical object or feature and wherein the annotated image 42 shall be displayed on the display unit 20. In order to improve the precision of the alignment, the contour of the two-dimensional segmentation model 50 is adapted to the ultrasound data 30 by deformation of the contour as schematically shown by an arrow 54 in FIG. 5.

Hence, the segmentation model can be adapted to the ultrasound image data 30 with low computation effort and within a short time frame so that also live ultrasound image data can be utilized for the respective definition or annotation of features of anatomical objects in the field of view.

Figure 6:
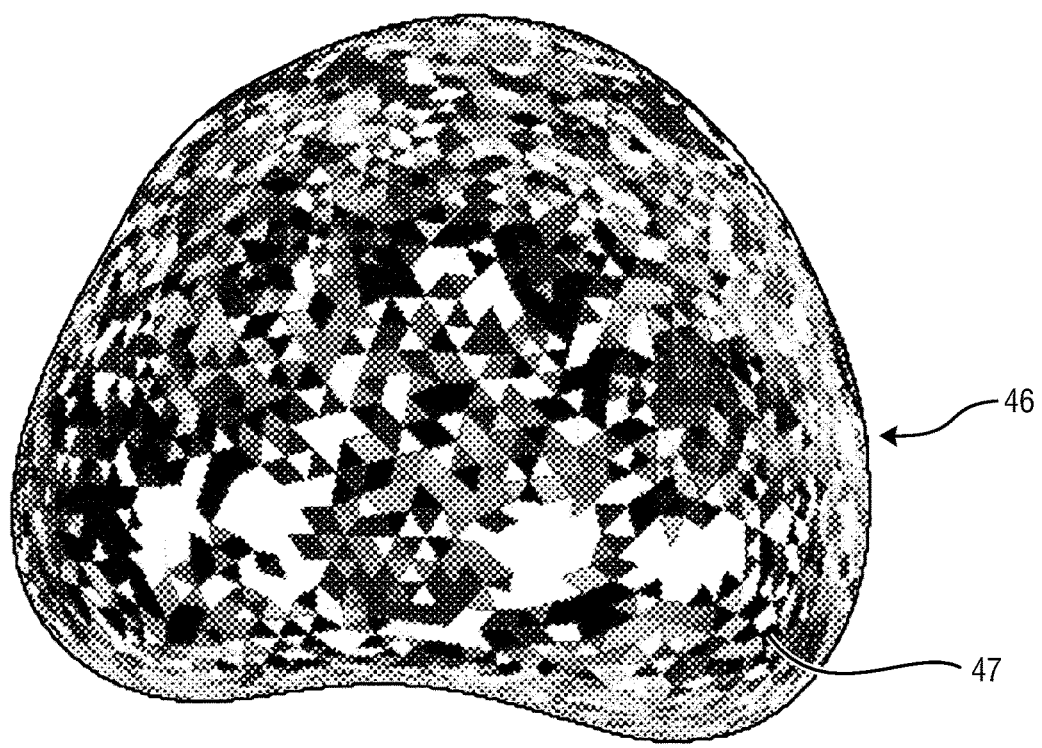
FIG. 6 shows a detailed diagram of segmentation model forming a three-dimensional representation of an anatomical object together with additional information about anatomical features and/or pattern recognition.
Figure 7:
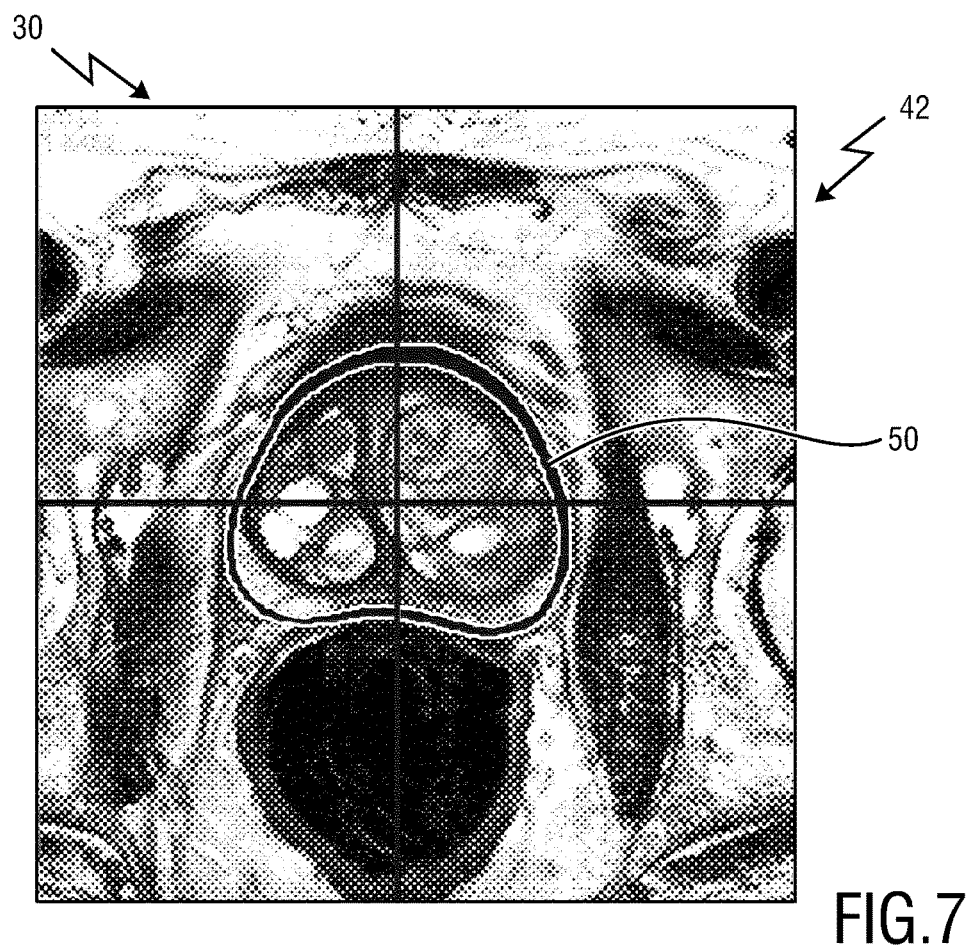
FIG. 7 shows an alignment of two-dimensional segmentation model and medical image data to segment an anatomical object in the field of view.

In FIG. 6, the three-dimensional segmentation model 46 is shown as a three-dimensional mesh of triangles 47, wherein each triangle 47 comprises different anatomical information, pattern information and/or boundary information for the respective alignment to the image data. On basis of this detailed three-dimensional segmentation model 46, the two-dimensional segmentation model 50 is derived and its contour can be aligned to the respective pattern in the ultrasound data 30 and superimposed in order to provide the annotated image 42 as shown in FIG. 7.

Figure 8:
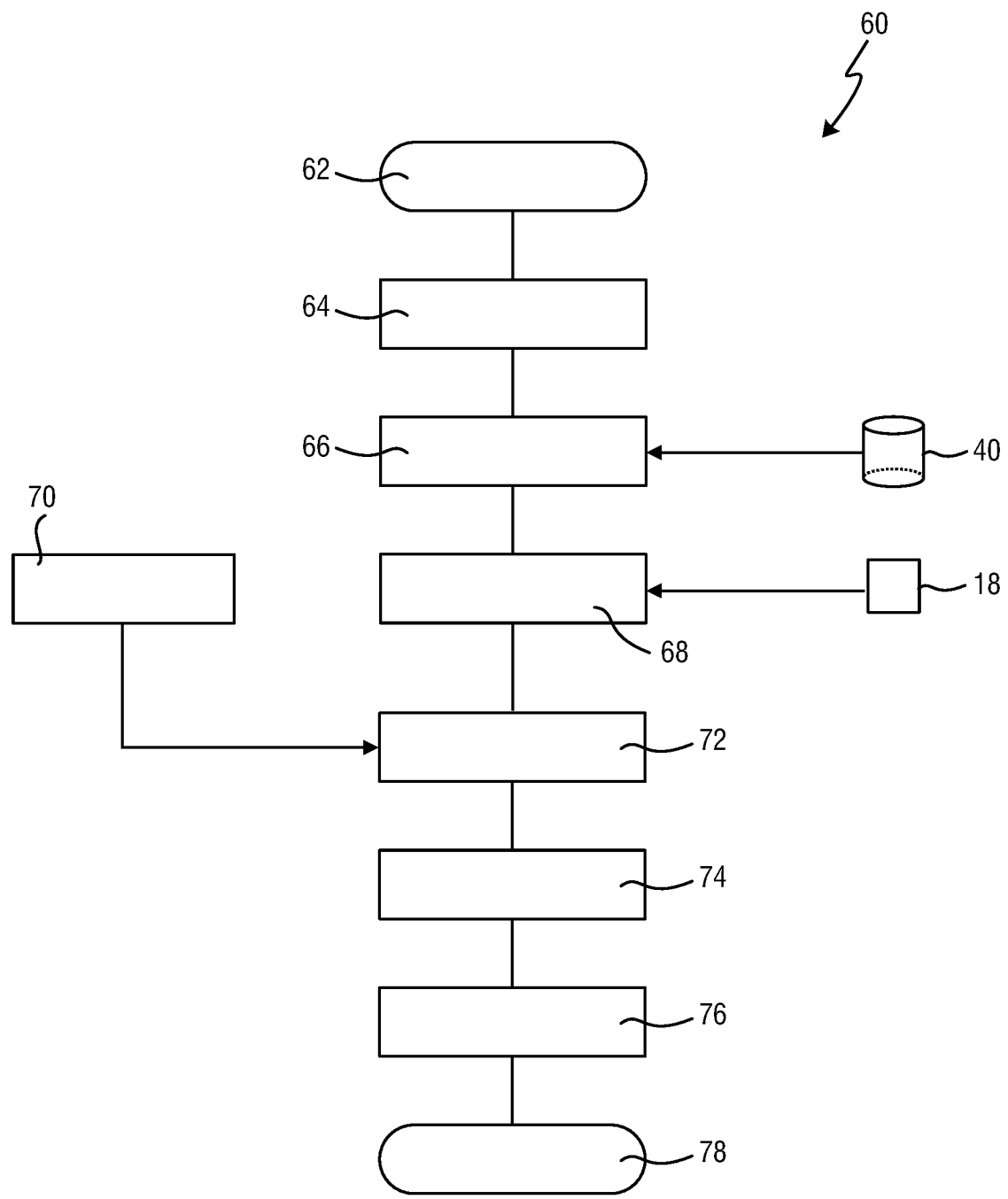
FIG. 8 shows a schematic flow diagram of a method for segmenting an object in the field of view of an ultrasound acquisition unit.

In FIG. 8 a schematic flow diagram illustrates a method for segmenting an anatomical object in the field of view 29 of the ultrasound acquisition unit 14. The method is generally denoted by 60. The method 60 starts at step 62. At step 64, the predefined three-dimensional model is provided to the segmentation unit 36 and at step 66 the segmentation unit 36 adapts the predefined three-dimensional segmentation model on the basis of the three-dimensional medical image data received from the database 40 or the imaging apparatus 40. The three-dimensional segmentation model 46 is determined as a result of the adaption of the predefined segmentation model to the respective anatomical features of the patient 12 derived from the three-dimensional medical image data.

In step 68, the image processor 34 receives the adapted three-dimensional segmentation model 46 from the segmentation unit 36 and the segmentation plane 48 from the position determining unit 18 and determines the two-dimensional segmentation model 50 by cutting or intersecting the adapted three-dimensional segmentation model 46. At step 70, the transducer array 26 captures the ultrasound data 30 and provides the ultrasound data 30 to the image processor 34, wherein the image processor 34 combines the adapted two-dimensional segmentation model 50 and the ultrasound image data 30 at step 72. At step 74 the image processor 34 adapts the two-dimensional segmentation model 50 to the anatomical object in the ultrasound data 30 on the basis of pattern detection in the ultrasound data 30 and combines the so adapted segmentation model and the image data to the annotated or labeled image 42, wherein in step 76, the annotated image data 42 is displayed by the display unit 20. At step 78, the method 60 ends.

Hence, the anatomical object in the field of view 29 of the ultrasound probe 14 can be identified with low computational effort and reduced time consumption so that anatomical objects can be segmented in live ultrasound images.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

The computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging apparatus for segmenting an anatomical object in a field of view of an ultrasound probe during an image-guided intervention, comprising:
   a first data interface configured to receive a continuous two-dimensional (2D) ultrasound data stream, provided as live image data, of the anatomical object in the field of view in an image plane from the ultrasound probe, wherein the first data interface is further configured to receive a three-dimensional segmentation model as a three-dimensional representation of the anatomical object,
   an image processor configured to generate a sequence of 2D images from the live image data, wherein the image processor is configured, for each 2D image of the sequence of 2D images, to determine a two-dimensional segmentation model from the three-dimensional segmentation model at a segmentation plane that corresponds to an image plane of the respective 2D image of the sequence of 2D images,
   adapt a contour of the two-dimensional segmentation model to the respective 2D image of the sequence of 2D images on the basis of pattern detection, and superposing the contour of the adapted two-dimensional segmentation model on the respective 2D image of the sequence of 2D images to generate annotated two-dimensional live image data, and wherein the image processor is further configured to provide the annotated two-dimensional live image data on a display.

2. An ultrasound imaging apparatus as claimed in claim 1, further comprising a second data interface configured to receive three-dimensional medical image data of the object for adapting the three-dimensional segmentation model of the anatomical object on the basis of the three-dimensional medical image data prior to the image-guided intervention.

3. An ultrasound imaging apparatus as claimed in claim 1, wherein the three-dimensional segmentation model and/or the two-dimensional segmentation model include a plurality of surface elements or line elements forming the representation of the anatomical object surface or contour and wherein anatomical information and/or pattern information are assigned to the surface elements or line elements.

4. An ultrasound imaging apparatus as claimed in claim 3, wherein the image processor is configured to adapt a contour of the two-dimensional segmentation model to the ultrasound data on the basis of pattern information.

5. An ultrasound imaging apparatus as claimed in claim 3, wherein the pattern information comprise ultrasound data intensity information of the object and wherein the image processor is configured to adapt a contour of the two-dimensional segmentation model to corresponding intensities in the continuous two-dimensional ultrasound data stream.

6. An ultrasound imaging apparatus as claimed in claim 3, wherein the image processor is configured to display the anatomical information in the annotated two-dimensional live image data.

7. An ultrasound imaging apparatus as claimed in claim 1, further comprising a position sensor for determining a position and a viewing direction of the ultrasound probe and for determining the image plane of the continuous two-dimensional ultrasound data stream, wherein the image processor is configured to determine the segmentation plane corresponding to the determined image plane.

8. An ultrasound imaging apparatus as claimed in claim 1, wherein the segmentation plane is predefined in relation to the three-dimensional segmentation model and wherein the image plane is adapted to the predefined segmentation plane.

9. An ultrasound imaging apparatus as claimed in claim 8, further comprising a user interface, wherein the segmentation plane is predefined by the user via the user interface.

10. A method for identifying an anatomical object in a field of view of an ultrasound probe during image-guided intervention, comprising the steps of:
    receiving a continuous two-dimensional (2D) ultrasound data stream, provided as live image data, in an image plane of the object in the field of view from the probe;
    receiving a three-dimensional segmentation model as a three-dimensional representation of the object,
    generating a sequence of 2D images from the live image data,
    determining a two-dimensional segmentation model from the three-dimensional segmentation model, for each 2D image of the sequence of 2D images, at a segmentation plane that corresponds to an image plane of a respective 2D image of the sequence of 2D images,
    deforming a contour of the two-dimensional segmentation model to the respective 2D image of the sequence of 2D images on the basis of pattern detection,
    superposing the contour of the two-dimensional segmentation model on the respective 2D image of the sequence of 2D images to generate annotated two-dimensional live image data, and
    providing the annotated two-dimensional live image data on a display.

11. A non-transitory computer readable medium configured to carry out the steps of the method as claimed in claim 10 when said computer program is carried out on a computer.

* * * * *